United States Patent [19]
Addison

[11] 4,157,355
[45] Jun. 5, 1979

[54] COMBINATION PROCESS FOR SELECTED AROMATIC HYDROCARBON PRODUCTION

[75] Inventor: George E. Addison, Mt. Prospect, Ill.

[73] Assignee: UOP Inc., Des Plaines, Ill.

[21] Appl. No.: 886,315

[22] Filed: Mar. 13, 1978

[51] Int. Cl.² ............................................. C07C 3/58
[52] U.S. Cl. ..................................... 585/321; 208/66; 585/322; 585/413; 585/483
[58] Field of Search ...................... 208/66; 260/672 R

[56] References Cited

U.S. PATENT DOCUMENTS

| | | | |
|---|---|---|---|
| 3,027,413 | 3/1962 | Moy et al. ............................... | 208/66 |
| 3,197,523 | 7/1965 | Michallco et al. ................ | 260/672 R |
| 3,204,007 | 8/1965 | Mukai et al. ....................... | 260/672 R |
| 3,371,126 | 2/1968 | Carson .............................. | 260/672 R |
| 3,536,771 | 10/1970 | DeGraff ............................. | 260/672 R |
| 3,625,879 | 12/1971 | Horne et al. ....................... | 260/672 R |
| 3,706,536 | 12/1972 | Greenwood et al. .......... | 260/672 R |
| 3,763,260 | 10/1973 | Pollitzer .......................... | 260/672 R |
| 3,780,122 | 12/1973 | Pollitzer .......................... | 260/672 R |
| 3,864,240 | 2/1975 | Stone ..................................... | 208/64 |
| 4,053,388 | 10/1977 | Bailey .............................. | 260/672 R |

Primary Examiner—C. Davis
Attorney, Agent, or Firm—James R. Hoatson, Jr.; Robert W. Erickson; William H. Page, II

[57] ABSTRACT

Selected aromatic hydrocarbon concentrates—benzene, mixed xylenes, etc.—are produced by way of a combination process which involves catalytic reforming followed by hot flash separation and dealkylation of the separated hot flash liquid phase. Although the process affords flexibility respecting the precise aromatic concentrate produced, it is particularly directed toward the maximization of benzene.

10 Claims, 1 Drawing Figure

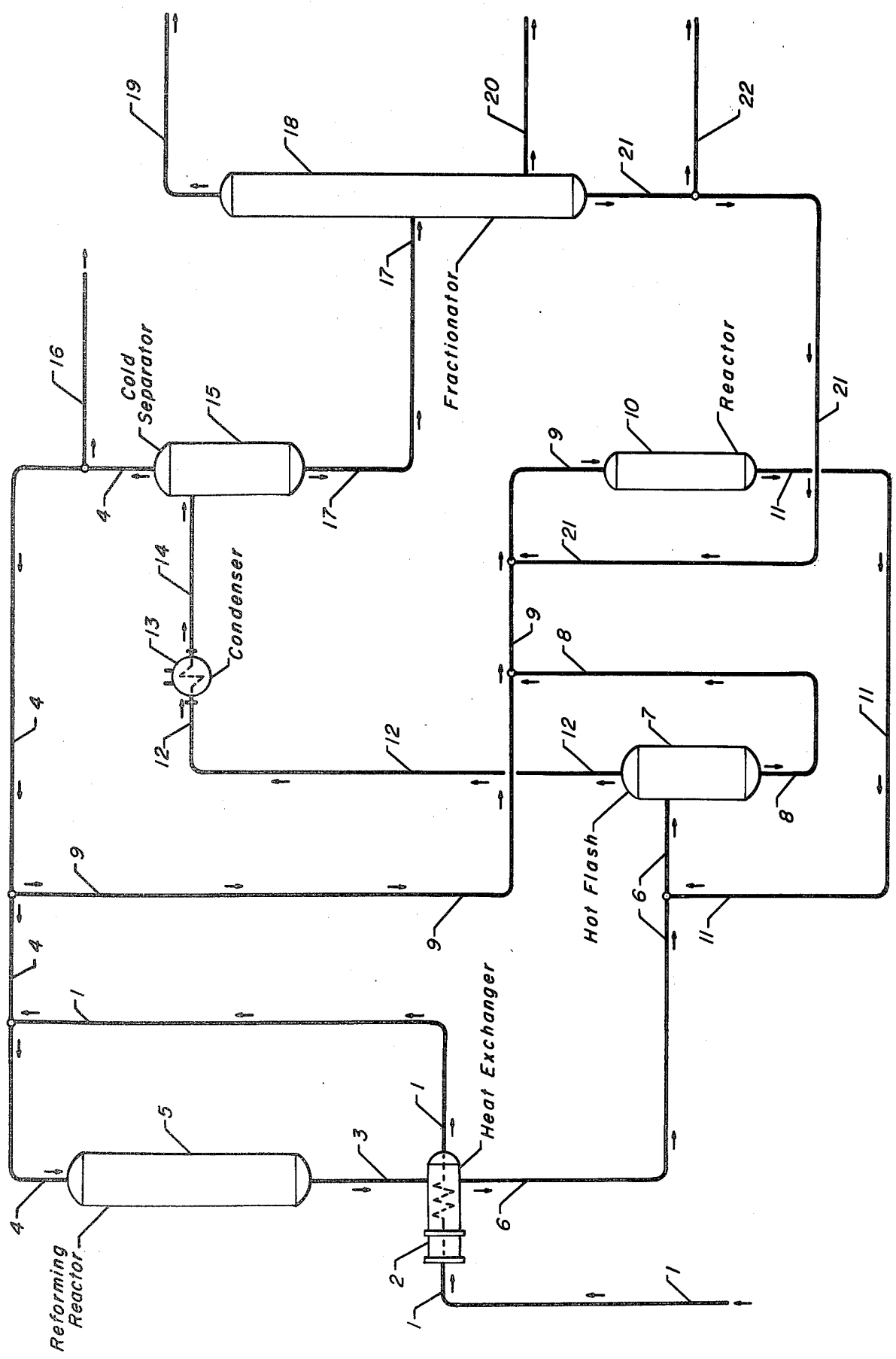

COMBINATION PROCESS FOR SELECTED AROMATIC HYDROCARBON PRODUCTION

APPLICABILITY OF INVENTION

As herein described, the present invention relates to a combination process which encompasses catalytic reforming for the conversion of naphthenes and paraffins to aromatics, and dealkylation of alkylaromatics to produce aromatic hydrocarbons having a different number of alkyl substituents. Hydrocarbons classified as aromatics have enjoyed a continually increasing demand within the market place due principally to their versatility as gasoline blending components and in the production of a wide spectrum of various petrochemical compounds. Aside from its use as a component of motor fuel, benzene serves as the starting material for the production of styrene, phenol, synthetic detergents, DDT and nylon intermediates; principal uses also include fumigants, insecticides and various solvents. The principal use of ethylbenzene, which may be derived by the alkylation of benzene, resides in steam dehydrogenation to produce styrene. Toluene is employed in aviation gasoline and as high-octane blending stocks; as a petrochemical raw material, it is used in the production of solvents, gums, resins, rubber cement, vinyl organosols and other organic chemicals. Mixed xylenes are primarily used in aviation gasoline and as solvent for alkyd resins, lacquers, enamels and rubber cements, etc. Relatively recently, para-xylene has been in great demand for use in the production of terephthalic acid which is employed in producing synthetic resins and fibers. Cymenes likewise are utilized as solvents and in synthetic resin manufacture; currently, para-cymene is in great demand for the production of para-cresol.

Fresh feed charge stocks for use herein are normally liquid hydrocarbons boiling within the gasoline, or naphtha boiling range; that is, hydrocarbons which exist in the liquid state at one atmosphere of pressure and a temperature of about 60° F., and which have normal boiling points up to about 425° F. Thus, it is contemplated that suitable charge stocks will include, but not by way of specific limitation, full boiling range naphthas (about 100° F. to about 400° F.), light naphthas (about 100° F. to about 200° F.) and heavy naphthas (about 20° F. to about 400° F.). As hereinafter indicated in greater detail, the charge stock is initially reacted with hydrogen in a catalytic reforming reaction zone, in contact therein with a Group VIII noble metal catalyst and at reforming conditions which foster the conversion of naphthenes and paraffins to aromatic hydrocarbons. Operating conditions are at a relatively high severity level in order to maximize the conversion to aromatics. At least a portion, but preferably all of the resulting catalytically reformed product effluent is separated in a hot flash zone. The hot flash liquid phase is reacted in a dealkylation reaction zone at conditions which are selected to dealkylate alkyl-substituted aromatic hydrocarbons. Product effluent from the dealkylation reaction zone is introduced into the hot flash separation zone, and the intended aromatic concentrate is recovered from the resulting hot flash vaporous phase. Alkylaromatics which boil above the desired aromatic concentrate are separately recovered and recycled to the dealkylation zone.

In the present specification and the appended claims, the use of the term "dealkylation" is intended to include both simple dealkylation—e.g. toluene and mixed xylenes are dealkylated to benzene—and transalkylation where toluene is transalkylated to produce a product mixture of benzene and xylenes. As hereinbefore stated, the present combination process is primarily intended for the maximum production of benzene.

OBJECTS AND EMBODIMENTS

A principal object of my invention is to provide a process for the production of a selected aromatic hydrocarbon concentrate. A corollary objective resides in a combination process for maximizing the production of benzene.

A more specific object is directed toward the combination of catalytic reforming and dealkylation, effected in a manner which results in an economically enhanced process for aromatic hydrocarbon production and recovery.

Therefore, one embodiment of the invention herein described is directed toward a combination process for the production of a selected aromatic hydrocarbon concentrate which comprises the sequential steps of: (a) reacting a hydrocarbonaceous charge stock and hydrogen in a catalytic reforming first reaction zone, at reforming conditions selected to convert paraffins and naphthenes to aromatic hydrocarbons; (b) separating the resulting first reaction zone effluent, in a first separation zone, at a temperature not substantially exceeding about 400° F. and a reduced pressure to provide (i) a first vaporous phase containing said selected aromatic hydrocarbon concentrate and, (ii) a first liquid phase containing higher boiling, alkylaromatic hydrocarbons; (c) reacting said first liquid phase in a dealkylation second reaction zone, at dealkylation conditions selected to dealkylate said alkylaromatic hydrocarbons; (d) introducing the resulting second reaction zone effluent into said first separation zone; (e) separating said first vaporous phase, in a second separation zone, at substantially the same pressure and a lower temperature in the range of about 60° F. to about 140° F., to provide (i) a hydrogen-rich second vaporous phase and, (ii) a second liquid phase containing substantially all of said aromatic concentrate; (f) recycling at least a portion of said hydrogen-rich second vaporous phase to said first reaction zone; and, (g) separating said second liquid phase, in a third separation zone, (i) to recover said selected aromatic hydrocarbon concentrate and, (ii) to provide a concentrated stream of higher boiling aromatic hydrocarbons.

In another embodiment, the concentrated stream of higher boiling aromatic hydrocarbons is recycled for introduction into the dealkylation second reaction zone.

These, as well as other objects and embodiments of the present invention, will become evident from the following, more detailed description thereof. In one such other embodiment, the charge stock is a naphtha fraction having an end boiling point lower than about 400° F.

CITATION OF RELEVANT PRIOR ART

As hereinbefore stated, my inventive concept encompasses the combination process of (1) catalytic reforming for the conversion of naphthenes and paraffins to aromatic hydrocarbons and, (2) dealkylation of the resulting reformed product effluent to produce selected aromatics having a different number of alkyl substituents. Essentially, the combination of these two processes encompasses a unique separation technique for the recovery of the desired product. Therefore, no claim is made herein to the individual processes other than the use thereof in combination with the product separation technique.

Briefly, the present combination process is effected by initially reacting a naphtha boiling range feedstock and hydrogen in a catalytic reforming first reaction zone. Reforming conditions, hereinafter specifically delineated, are selected to convert the normally liquid hydrocarbons into aromatics—via dehydrogenation and dehydrocyclization—with the concomitant production of hydrogen. Preferably, the entire as-produced reforming zone effluent is introduced into a hot flash zone, the liquid phase from which serves as the charge to a dealkylation second reaction zone maintained at dealkylation conditions which convert alkylaromatics to aromatic hydrocarbons having a lesser number of alkyl substituents. Thus, toluene and mixed xylenes may be dealkylated for maximum benzene recovery, or toluene may be transalkylated for the purpose of maximizing both benzene and mixed xylenes. In the former situation, a greater quantity of light ends, especially methane, is co-produced, relative to the amount resulting from transalkylation.

The dealkylation reaction zone effluent is introduced into the hot flash separation zone for recovery of additional selected aromatics in the hot flash vapors. Provided, therefore, are (1) a first vaporous phase containing the selected aromatic concentrate and some higher boiling aromatic hydrocarbons and, (2) a first liquid phase containing the greater proportion of higher boiling aromatic hydrocarbons. The latter is recycled to the dealkylation reaction zone while the former is introduced into a second separation zone at substantially the same pressure and a lower temperature in the range of about 60° F. to about 140° F. (commonly referred to as cold, high-pressure separation) to provide (1) a hydrogen-rich second vaporous phase and, (2) a second liquid phase containing the selected aromatic concentrate. At least a portion of the hydrogen-rich vaporous phase is recycled to the catalytic reforming reaction zone; a second portion may be recycled to the dealkylation reaction zone. The second liquid phase is separated, preferably by fractional distillation, to remove various light ends and to recover the selected aromatic concentrate, higher boiling aromatic hydrocarbons, withdrawn as a bottoms fraction, are preferably recycled to the dealkylation reaction zone.

It is recognized and acknowledged that many illustrations of catalytic reforming, both the traditional fixed-bed system and the more recent stacked system, through which the catalyst particles are downwardly movable via gravity-flow, are to be found in the prior art. Similarly, the published literature is replete with examples of processes for the dealkylation and/or transalkylation of alkyl-substituted aromatic hydrocarbons. Any attempt to delineate exhaustively the appropriate prior art would be an exercise in futility. Therefore, only two examples of each will be discussed. Since the present technique involves a combination of these two processes, it is believed that the most relevant prior art will be directed toward catalytic reforming followed by dealkylation. Copies of the prior art hereinbelow delineated accompany this application.

The catalytic reforming section of the present combination process may utilize a plurality of radialflow, fixed-bed reaction zones, a stacked system wherein the catalyst particles are downwardly movable, from one reaction zone to the next succeeding reaction zone, via gravity-flow, or a combination of fixed-bed with the gravity-flowing catalyst system. U.S. Pat. No. 3,706,536 (Cl. 23-288G), issued Dec. 19, 1972, is illustrative of a stacked reactor system in which each reaction zone contains an annular-form catalyst bed through which the reactant stream flows laterally and radially, while the catalyst particles flow downwardly from one reaction zone to the next succeeding lower reaction zone. Catalyst particles withdrawn from the last or lowermost zone are transported to the top of the regeneration tower; regenerated catalyst particles are transported and introduced into the uppermost reaction zone in the stacked system.

U.S. Pat. No. 3,864,240 (Cl. 208-64), issued Feb. 4, 1975, is illustrative of the integration of a reaction system having gravity-flowing catalyst particles with a fixed-bed system. At least periodically, catalyst particles are withdrawn from the former and transported to the top of a regeneration facility in which they assume the form of a single descending column. Regenerated catalyst particles are subsequently transported to the top of the gravity-flowing reaction zone.

As those possessing the requisite skill in the appropriate art are aware, the described continuous catalyst regeneration reforming system offers numerous advantages when compared to the conventional fixed-bed prior art systems. Among these is the capability of efficient operation at comparatively lower pressures and higher liquid hourly space velocities. With continuous catalyst regeneration, higher consistent inlet catalyst bed temperatures can be maintained, and there is a corresponding increase in both hydrogen production and the purity thereof within the recycled vaporous phase.

Dealkylation of alkylaromatic hydrocarbons, in a catalytic system, is disclosed in U.S. Pat. No. 3,197,523 (Cl. 260–672), issued July 27, 1965. Suitable alkylaromatic feedstocks are those comprising toluene, mixed xylenes, ethylbenzene, mixed diethylbenzenes and various alkyl-substituted naphthalenes. Catalysts utilized in the process contain at least one oxide of tin, titanium and zirconium combined with at least one oxide of chromium, molybdenum and tungsten. Disclosed operating conditions include temperatures in the range of about 1000° F. to about 1500° F. and pressures from about 300 psig. to about 1000 psig.

Another hydrodealkylation technique is described in U.S. Pat. No. 3,204,007 (Cl. 260–672), issued Aug. 31, 1965; the process is particularly directed toward the production and recovery of non-substituted aromatic hydrocarbons, principally benzene and/or naphthalene. Hydrodealkylated product effluent is cooled by being initially utilized as a heat-exchange medium (to preheat fresh feed to the direct-fired heater) and then passed into a cooler/condenser (9). Cooled effluent traverses three flash drums, the liquid phase passing therethrough in series. The three flash drums function at succeedingly lower pressures of 500 psig. to 600 psig. (12), 50 psig. to 150 psig. (22) and atmospheric pressures (31). In view of the intentional cooling and condensing of the dealkylated product effluent, these three zones are considered "cold flash separators" as distinguished from a "hot flash zone".

Operating conditions include temperatures from about 1000° F. to 1500° F., pressures in the range of about 300 psig. to about 600 psig., a liquid hourly space velocity of 0.1 to 20.0 (preferably 0.5 to 5.0) and a hydrogen to hydrocarbon fresh feed mole ratio of about 8.7:1.0 (refer to Example 1). Catalysts comprise metals from the platinum group, cesium, tungsten, silver, rhenium and chromium combined with a high surface area carrier material.

Transalkylation of alkylaromatic hydrocarbons constitutes the subject of U.S. Pat. No. 3,763,260 (Cl. 260-672T), issued Oct. 2, 1973. Here the catalytic composite constitutes a metal component selected from the group of copper, silver and zirconium combined with zeolitic mordenite having a silica/alumina mole ratio of at least 40.0:1.0. Such catalysts are utilized for hydrocarbon transalkylation reactions at temperatures from 0° C. to about 500° C. (32° F. to about 932° F.) and pressures from about atmospheric to about 1500 psig. Applicable reactions include transalkylation of toluene to produce benzene and mixed xylenes, transalkylation of toluene with $C_9$-methyl aromatics to produce xylenes and transalkylation of benzene with polyethylbenzene to produce ethylbenzene. U.S. Pat. No. 3,780,122 (Cl. 260-672T), issued Dec. 18, 1973 is believed to be cumulative to the foregoing, the exception being a lack of disclosure of metallic components being combined with the zeolitic mordenite.

A combination process of catalytic reforming and dealkylation is presented in U.S. Pat. No. 3,371,126 (Cl. 260-672), issued Feb. 27, 1968. This is additionally combined with both a hydrogen-producing plant (via steam reforming of naphtha) and a hydrogen purification system (via cryogenic techniques). Principally, the objective of this process resides in the simultaneous production of benzene-type hydrocarbons and town gas of a predetermined calorific value. The catalytic reforming and dealkylation reaction zones function in series with the total effluent from the former being directly introduced into the latter. Dealkylation reaction product effluent is withdrawn and condensed (column 6, lines 70-71), and introduced into a cold separator (24) for separation into normally vaporous components and normally liquid components from which benzene is recovered via fractionation. Clearly, there is a lack of recognition respecting the use of a hot flash zone to separate the reforming zone product effluent. Further, there exists no teaching of introducing the hot flash vaporous phase into a cold separator.

It is believed that the foregoing, taken either singularly or in combination, neither anticipates, nor renders the present invention, as described and claimed herein, obvious.

SUMMARY OF INVENTION

Essentially, the combination process encompassed by my inventive concept involves two reaction systems, catalytic reforming and dealkylation (or transalkylation) and a three-step separation facility for the ultimately desired product recovery. The separation facility consists of a hot flash zone, a cold separator into which condensed hot flash vapors are introduced and a fractionation facility which recovers the desired product from the cold separator liquid phase.

As hereinbefore stated, the catalytic reforming, system may function with a plurality of fixed-bed zones, with a plurality of stacked zones through which catalyst particles flow via gravity, or a combination thereof as described in the previously discussed U.S. Pat. No. 3,864,240. Since aromatic hydrocarbon production, via dehydrogenation of naphthenes and especially dehydrocyclization of paraffins, is favored by a relatively high-severity operation—e.g. higher temperatures and lower pressures—the continuous catalyst regeneration reforming system is particularly preferred. This preference stems from the fact that a higher carbon (often referred to as "coke") level can be tolerated on the catalytic composites. Similarly, a mixed system wherein the naphtha charge stock is first serially reformed in two or more fixed-bed zones, followed by one or more zones in the stacked, gravity-flowing configuration, may be utilized. The latter has the further advantage in affording the utilization of two different catalysts which permits the overall reforming process to be "tailored" to achieve the desired reformed product.

Catalytic reforming of naphtha boiling range hydrocarbons is a vapor-phase operation, and is effected at conversion conditions including catalyst bed temperatures in the range of about 750° F. to about 1020° F.; judicious and cautious techniques generally dictate that catalyst temperatures not substantially exceed a level of about 1020° F. Other conditions include pressures in the range of about 50 psig. to about 1000° psig., a liquid hourly space velocity (defined as volumes of fresh charge stock per hour, per volume of total catalyst particles) in the range of about 0.5 to about 10.0 and a hydrogen to hydrocarbon mole ratio in the range of about 1.0:1.0 to about 15.0:1.0. As a practical matter, fixed-bed reforming systems necessitate lower catalyst bed temperatures from 750 ° F. to about 910° F., higher pressures from about 500 psig. to 1000 psig., lower space velocities of 0.5 to about 2.5 and higher hydrogen/hydrocarbon mole ratios of 4.5:1.0 to about 8.0:1.0. On the other hand, benefits accrue through continuous catalyst regeneration reforming in that the operating conditions involve higher catalyst bed temperatures from 950° F. to 1010° F., lower pressures of about 50 psig. to about 450 psig., higher space velocities of 3.0 to about 8.0 and lower hydrogen/hydrocarbon mole ratios of 0.5:1.0 to about 5.5:1.0.

Catalytic reforming reactions are varied, and include dehydrogenation of naphthenes to aromatics, dehydrocyclization of paraffins to aromatics, hydrocracking of long-chain paraffins into lower-boiling, normally liquid material and, to a certain extent, the isomerization of paraffins. These reactions, the net result of which is endothermicity with respect to the overall reaction system, are effected through the utilization of one or more Group VIII noble metals—e.g. platinum, palladium, rhodium, ruthenium, osmium and iridium—combined with a halogen, generally chlorine and/or fluorine, and a porous carrier material such as gamma alumina. Relatively recent investigative developments have indicated that unexpected advantageous results are attainable and enjoyed through the cojoint utilization of a catalytic modifier; these have been selected from the group of cobalt, nickel, gallium, germanium, tin, rhenium, vanadium, tungsten, zinc and mixtures thereof.

The precise operating conditions and catalytic composite utilized in the catalytic reforming section will be dependent upon both the physical and chemical characteristics of the naphtha boiling range charge stock, as well as upon the selected aromatic concentrate to be recovered. Therefore, it is understood that the viability of the present invention does not rely upon either catalyst composition, or operating conditions in the reforming section. The naphtha feedstock may be, and most generally is pre-heated via indirect heat-exchange with one or more high-temperature process streams. For the most part, such streams will include the effluent withdrawn from both the reforming and dealkylation sections; the latter will normally have the higher temperature. In any event, the charge stock is subsequently introduced into a direct-fired heater wherein its temperature is further increased to at least the level needed to provide the designed temperature at the inlet to the catalyst bed and the initial reaction zone. Since reforming reactions are generally endothermic, and reforming is effected in a plurality of individual zones, the temperature of the effluent from one zone will be increased in an interstage heater prior to passing into the next succeeding reaction zone.

In accordance with the present combination process, the catalytically reformed product effluent, preferably in total, is introduced into the hot flash separation zone at a temperature not substantially in excess of about 400° F. and at a reduced pressure. As above stated, the product effluent from the catalytic reforming section may be first employed as a pre-heat medium. Another such use would be to supply at least a portion of the heat necessary to effect the final fractional distillation for product recovery. Likewise, the dealkylation reaction zone effluent may serve to supply heat to the fresh feed charge stock, or to the feed to the fractionation facilities, either in and of itself, or in some "hot oil belt" combination with the reformed product effluent. The purpose of the hot flash zone is to provide (i) a vaporous phase containing all the selected aromatic concentrate first produced in the catalytic reforming system and, (ii) a normally liquid phase containing higher boiling aromatic hydrocarbons. Normally vaporous hydrocarbons, hydrogen and normally liquid material boiling below the selected aromatic hydrocarbons are also removed in the vaporous phase. The reduced pressure under which the hot flash zone functions is dependent upon the temperature at which the feed thereto is introduced. Considered also is the character of the aromatic hydrocarbons which are intended to be flashed and recovered in the vaporous phase.

The liquid phase from the hot flash separation zone is introduced into the dealkylation reaction zone in order to effect further conversion of alkylaromatics to the selected aromatic concentrate. Dealkylation operating conditions will generally be within the ranges suggested by the prior art previously delineated. As stated, these include temperatures within the range of about 1000° F. to about 1500° F. (believed to refer to the temperature at the inlet to the catalyst bed), pressures from about 300 psig. to about 1000 psig. and liquid hourly space velocities preferably in the range of about 0.5 to about 5.0. When utilizing zeolitic-based catalytic material, lower temperatures for transalkylation are afforded; in U.S. Pat. Nos. 3,763,260 and 3,780,122 (previously discussed), temperatures of 500° F. to 800° F. and 392° F. to 896° F. are respectively disclosed.

In contrast to catalytic reforming, which is an endothermic, hydrogen-producing reaction, dealkylation is an exothermic, hydrogen-consuming reaction. Consequently, the temperature of the reactant stream effluent exiting the dealkylation reaction zone will be considerably higher than the temperature at which the catalytically reformed product effluent is withdrawn from the reforming section. In those cases where the selected aromatic concentrate requires transalkylation to produce benzene and mixed xylenes from toluene, the exit temperature will be lower than that experienced when dealkylation is being effected to maximize benzene production. Regardless, the exothermic dealkylation, or transalkylation reactions may be effected in a plurality of reaction zones having intermediate cooling facilities in order to decrease the overall temperature differential. Such a technique is well known in the art of conducting exothermic reactions, and forms no essential feature of the present invention.

Suitable dealkylation and transalkylation catalysts, for utilization in the present combination process, include those alluded to in the previous discussion of the prior art. Such catalysts generally consist of one or more catalytically active metallic components combined with a suitable inorganic oxide carrier material. In many instances, the acidic function of the catalyst will be enhanced through the addition thereto of a halogen component, particularly a chlorine and/or fluorine component. Inorganic oxide carrier materials include both amorphous and zeolitic material, as well as mixtures thereof. When amorphous, the carrier is generally selected from the group of alumina, silica, zirconia, titania, hafnia, boria and various mixtures thereof. Zeolitic carriers are of the character of crystalline aluminosilicates, and include mordenite, Type X and Type Y molecular sieves; such zeolitic material may be incorporated within an amorphous matrix.

With respect to the metallic components, the selections are available from a large number. These too may be those of the prior art including tin, titanium, zirconium, chromium, molybdenum, tungsten, silver, copper, rhenium, and the noble metals of Group VIII, such as platinum, osmium, rhodium, ruthenium, iridium and palladium. From the practical viewpoint, the selection of the particular catalytic composite will be dependent upon the component analysis of the aromatic hydrocarbon portion of the reformed product effluent which is charged to the dealkylation reaction zone. Preferred for use herein, when the principal reactions involve dealkylation for maximum benzene, is gamma, or eta alumina containing a chromium component; for the transalkylation of toluene, to produce benzene and mixed xylenes, the use of zeolitic mordenite, which may be admixed within an amorphous matrix is preferred.

Vaporous material from the hot flash zone is cooled and condensed to a temperature generally in the range of about 60° F. to about 140° F., and introduced at substantially the same pressure into a cold separator. Normally gaseous hydrocarbons and hydrogen are removed as a vaporous phase; in some instances, this stream will contain a minor quantity of pentanes and hexanes. A portion of the gaseous material is vented from the system under pressure control, and at least another portion is recycled to the catalytic reforming system. Flexibility is afforded in that another portion can be diverted to the dealkylation reaction zone. The normally liquid phase from the cold separator will contain pentanes and heavier hydrocarbons, including substantially all of the desired aromatics, and some absorbed gaseous paraffins and hydrogen. The latter serves as a feed to a fractionation facility, from which the selected aromatic hydrocarbon fraction is removed as a heart-cut, lower boiling components are withdrawn as an overhead stream and the higher boiling aromatics as a bottoms fraction. In a preferred technique, at least a portion of this bottoms fraction is recycled to the dealkylation reaction zone. Alternatively, all of the bottoms fraction may be so recycled, or all may be withdrawn as a separate product of the process.

BRIEF DESCRIPTION OF DRAWING

Further description of the process encompassed by my inventive concept will be made in conjunction with the accompanying drawing, which is presented for the sole purpose of illustration, and not with the intent of limiting the invention beyond the scope and spirit of the appended claims. The drawing is shown as a simplified schematic flow diagram in which details such as pumps, instrumentation and other controls, coolers, condensers, compressors, heat-exchange and heat-recovery circuits, valving start-up lines and similar hardware have been eliminated or reduced in number as being non-essential to the understanding of the techniques involved. Utilization of these miscellaneous appurtenances, to modify the process as illustrated, will be evident to those possessing the requisite skill in the art of petroleum refining technology.

In the drawing, reforming reactor 5 will be described as a three-reaction zone, stacked system through which catalyst particles are movable via gravity-flow. The initial direct-fired charge heater and two catalyst bed inter-heaters are not illustrated. Similarly, reactor 10 constitutes the dealkylation reaction zone, and will be described as two series-flow chambers having cooling facilities therebetween.

DETAILED DESCRIPTION OF DRAWING

With specific reference now to the drawing, fresh feed charge stock, being a normally liquid naphtha fraction having an initial boiling point of about 180° F. and an end boiling point of about 390° F., is introduced into the process by way of conduit 1. This heavy naphtha fraction has been previously subjected to hydrotreating for olefinic hydrocarbon saturation, and for the removal of sulfurous and nitrogenous components. The charge stock is initially introduced into heat-exchanger 2 wherein it is preheated via indirect contact with reformed product effluent from line 3. Continuing through line 1, the fresh feed is admixed with a hydrogen-rich gaseous phase in line 4, in the amount such that the hydrogen/fresh feed mole ratio is about 2.5:1.0. The mixture continues through line 4, and is introduced thereby into reforming reactor system 5, after being increased in temperature to about 1000° F. As above set forth, the catalytic reforming is preferably effected in a stacked system, in which catalyst particles are downwardly-movable by way of gravity-flow, integrated with a continuous catalyst regeneration tower.

In this illustration, the stacked system consists of three individual reaction zones containing a catalytic composite of about 0.6% platinum, 0.5% tin and about 1.0% chlorine, by weight and calculated as the elements thereof; these catalytically active ingredients are combined with gamma alumina. The pressure at the inlet to the stacked system is about 420 psig., while at the outlet, the pressure is about 410 psig. The inlet temperature to each of the three beds of catalyst particles is maintained at about 990° F., and the overall liquid hourly space velocity approximates 1.6. Catalytically reformed effluent is withdrawn by way of conduit 3 and is employed as the heat-exchange medium in exchanger 2. The cooled effluent is withdrawn through line 6 and admixed with dealkylation product effluent from line 11. The mixture continues through line 6, and is introduced thereby into hot flash separation zone 7 at a temperature in the range of about 250° F. to about 350° F. and a pressure of about 200 psig.

In this particular situation, the intent is to maximize the production of benzene from the heavy naphtha charge stock. Therefore, hot flash separation zone 7 will function to produce (i) a vaporous phase in line 12 which contains substantially all the benzene and lower-boiling hydrocarbons and, (ii) a liquid phase in line 8 which is combined with a portion of a hydrogen-rich gaseous phase in line 9, the mixture continuing through line 9 as the feed to dealkylation reaction zone 10. The catalytically reformed product effluent portion of the total feed to hot flash zone 7, excluding pentanes, normally vaporous hydrocarbons and hydrogen, has the approximate component stream analysis shown in the following Table I:

TABLE I

| Component | Normally Liquid Reformed Effluent | |
|---|---|---|
| | Bbl./day | Vol. % |
| Hexane | 264 | 2.33 |
| $C_7$–$C_9$ Paraffins | 1047 | 9.20 |
| Benzene | 466 | 4.10 |
| Toluene | 1309 | 11.51 |
| Mixed Xylenes | 2663 | 23.41 |
| Ethylbenzene | 597 | 5.25 |
| $C_9$—plus Aromatics | 5028 | 44.20 |

Dealkylation reaction system 7 contains a catalytic composite of 1.9% by weight of titanium oxide, 4.7% of tin oxide and about 15.0% of chromium oxide, combined with gamma alumina. In this illustration, the dealkylation reactions are effected at a catalyst bed inlet temperature of 1,200° F. and a pressure of about 400 psig. Exothermicity results in a catalyst bed outlet temperature of about 1,350° F.; therefore in the two-zone series system, the first zone effluent will be cooled to about 1,200° F. prior to being introduced into the second reaction zone. As previously set forth, hot flash separation zone serves to remove substantially all the benzene and lighter hydrocarbons as a vaporous phase in line 12. This phase will also contain an amount of the heavier aromatic hydrocarbons, much the same as the liquid phase in line 8 will contain some of the benzene and hexane. For the purposes of this illustration, it will be presumed that the hot flash zone liquid phase is substantially completely free from material boiling below toluene.

The hot flash liquid phase in line 8 is admixed with a hydrogen-rich gaseous phase in line 9, the mixture continuing therethrough into dealkylation reaction system 10. Dealkylation product effluent, at a temperature of about 1,350° F., is withdrawn via line 11; after its use as a heat-exchange medium and further cooling to a temperature of about 250° F. to about 350° F., the effluent is admixed with the reformed product effluent in line 6, and introduced therewith into hot flash zone 7. The vaporous phase in line 12, which now is inclusive of the benzene and lower-boiling material produced via dealkylation, is introduced into cooler/condenser 13, wherein the temperature is lowered to a level in the range of 60° F. to about 140° F.—e.g. 90° F. The thus-condensed vaporous phase passes through conduit 14 into cold separator 15 at a pressure of about 190 psig.

A hydrogen-rich vaporous phase is recovered via line 4, and a portion thereof is vented from the process by way of conduit 16. The remainder may be subjected to cryogenic separation in order to increase the hydrogen purity prior to being recycled to the catalytic reforming system. Preferably, a second portion of the recycled hydrogen-rich phase is diverted via line 9 for introduction into dealkylation system 10. The amount so diverted should be such that hydrogen is present in excess of that which will be consumed during the dealkylation reactions. Condensed liquid material is introduced through conduit 17 into a fractionation facility 18. Fractional distillation conditions of temperature and pressure are such that hexanes and lower-boiling hydrocarbons are withdrawn as an overhead stream through conduit 19; benzene concentrate is withdrawn as a heart-cut in line 20. Heavier aromatic hydrocarbons are recovered as a bottoms stream through line 21, and recycled thereby into dealkylation reactor 10. Where either desirable, or necessary to prevent the buildup of a refractory component in the recycled material, a drag stream may be withdrawn from the process through line 22.

In the following Table II, the material balance respecting only the dealkylation system is presented; the numerical values represent thousands of pounds per day. That is, the indicated yields do not include the 466 Bbl./day of benzene originally part of the reformed product effluent recovered in the vaporous phase from hot flash zone 10. Likewise, the tabulation does not include any material withdrawn or vented from the process through conduits 16, 19 and which was originally in the reformed effluent in line 3, and/or conduit 22.

TABLE II

| | Dealkylation Material Balance | | | |
|---|---|---|---|---|
| Component | Feed | Reactor Effluent | Recycle | Net |
| Hydrogen | 153.3* | — | — | — |
| Methane | — | 1238.2 | — | 1238.2 |
| Ethane | — | 12.8 | — | 12.8 |
| Benzene | — | 2001.8 | — | 2001.8 |
| Toluene | 399.5 | 326.2 | 326.2 | — |
| $C_8$—Aromatics | 996.2 | 70.2 | 70.2 | — |
| $C_9$—Aromatics | 1443.6 | 6.0 | 6.0 | — |
| $C_7$—$C_9$ Paraffins | 260.2 | — | — | — |

*Hydrogen consumed in dealkylation reactions.

The foregoing specification, particularly when read in conjunction with the accompanying drawing, is believed to present a clear understanding of the present invention, the scope of which is defined by the appended claims.

I claim as my invention:

1. A combination process for the production of a selected aromatic hydrocarbon concentrate which comprises the sequential steps of:
    (a) reacting a hydrocarbonaceous charge stock and hydrogen in a catalytic reforming first reaction zone, at reforming conditions selected to convert paraffins and naphthenes to aromatic hydrocarbons;
    (b) separating the resulting first reaction zone effluent, in a first separation zone, at a temperature of at least 250° F. but not substantially exceeding about 400° F. and a reduced pressure to provide (i) a first vaporous phase containing said selected aromatic hydrocarbon concentrate and, (ii) a first liquid phase containing higher boiling, alkylaromatic hydrocarbons;
    (c) reacting said first liquid phase in a dealkylation second reaction zone, at dealkylation conditions selected to dealkylate said alkylaromatic hydrocarbons;
    (d) introducing the resulting second reaction zone effluent into said first separation zone;
    (e) separating said first vaporous phase, in a second separation zone, at substantially the same pressure and a lower temperature in the range of about 60° F. to about 140° F., to provide (i) a hydrogen-rich second vaporous phase and, (ii) a second liquid phase containing substantially all of said aromatic concentrate;
    (f) recycling at least a portion of said hydrogen-rich second vaporous phase to said first reaction zone; and,
    (g) separating said second liquid phase, in a third separation zone, (i) to recover said selected aromatic concentrate and, (ii) to provide a concentrated stream of higher boiling aromatic hydrocarbons.

2. The process of claim 1 further characterized in that said higher boiling aromatic hydrocarbons are introduced into said second reaction zone.

3. The process of claim 2 further characterized in that at least a portion of said hydrogen-rich second vaporous phase is introduced into said second reaction zone.

4. The process of claim 1 further characterized in that said hydrocarbonaceous charge stock consists of normally liquid hydrocarbons boiling up to about 425° F.

5. The process of claim 1 further characterized in that said charge stock is a naphtha having an end boiling point lower than about 400° F.

6. The process of claim 1 further characterized in that said selected aromatic hydrocarbon concentrate is benzene.

7. The process of claim 6 further characterized in that said concentrated stream of higher boiling aromatic hydrocarbons is introduced into said second reaction zone.

8. The process of claim 1 further characterized in that said selected aromatic concentrate comprises benzene, toluene and xylene.

9. The process of claim 8 further characterized in that said concentrated stream of higher boiling aromatic hydrocarbons is introduced into said second reaction zone.

10. The process of claim 1 further characterized in that said selected aromatic concentrate is benzene, a first portion of said higher boiling aromatic hydrocarbons is separately recovered and a second portion is introduced into said second reaction zone.

* * * * *